United States Patent
Suh et al.

(10) Patent No.: US 7,087,103 B2
(45) Date of Patent: Aug. 8, 2006

(54) METHOD OF USING GAS PRESSURE TO REDUCE POROSITY IN COMPOSITE MATERIALS

(75) Inventors: Byoung I. Suh, Oak Brook, IL (US); Steven J. Duray, Rolling Meadows, IL (US)

(73) Assignee: Bisco, Inc., Schaumburg, IL (US)

( * ) Notice: Subject to any disclaimer, the term of this patent is extended or adjusted under 35 U.S.C. 154(b) by 320 days.

(21) Appl. No.: 10/192,222

(22) Filed: Jul. 10, 2002

(65) Prior Publication Data

US 2004/0008569 A1 Jan. 15, 2004

(51) Int. Cl.
*B01D 19/00* (2006.01)
*A61K 6/08* (2006.01)

(52) U.S. Cl. ............................. 95/241; 95/243; 106/35
(58) Field of Classification Search ............ 95/241, 95/243, 266, 247; 96/155; 106/35
See application file for complete search history.

(56) References Cited

U.S. PATENT DOCUMENTS

| 4,521,191 | A | | 6/1985 | Ehrnford .................... 433/164 |
|---|---|---|---|---|
| 4,952,530 | A | | 8/1990 | Brosnan et al. ............... 501/39 |
| 5,266,609 | A | * | 11/1993 | Hall et al. .................. 523/116 |
| 5,328,262 | A | | 7/1994 | Lidgren et al. ............. 366/139 |
| 5,348,475 | A | | 9/1994 | Waknine et al. ............ 433/215 |
| 5,750,590 | A | * | 5/1998 | Schaefer et al. ............ 523/115 |
| 6,376,397 | B1 | | 4/2002 | Petticrew ........................ 501/5 |
| 6,471,897 | B1 | | 10/2002 | Walsh et al. ................ 264/109 |
| 2003/0193119 | A1 | * | 10/2003 | Zychek et al. ............. 264/494 |

* cited by examiner

Primary Examiner—Frank M. Lawrence
Assistant Examiner—Douglas J. Theisen
(74) Attorney, Agent, or Firm—Ice Miller

(57) ABSTRACT

Methods for reducing the number and/or size of gas bubbles in a material are disclosed. The disclosed methods involve subjecting materials to pressure for a period of time. The methods have been found to be useful in the preparation of dental composites and dental structures prepared from those composites. Materials produced using the disclosed methods can have enhanced structural and/or aesthetic features.

38 Claims, 1 Drawing Sheet

METHOD OF USING GAS PRESSURE TO REDUCE POROSITY IN COMPOSITE MATERIALS

FIELD OF THE INVENTION

The invention relates to methods of reducing the amount and size of gas bubbles in materials and, more particularly, to methods of removing air bubbles from dental composite materials.

BACKGROUND OF THE INVENTION

Materials used in dental applications have several desirable structural properties. They are formable into a desired shape, yet become sufficiently strong when cured. The aesthetic properties of dental materials are also important. Composite materials, such as those having a filler component and a resin component, have been found to be useful in dental applications.

Air bubbles typically become trapped in the composite material during mixing of the composite material and in loading the material into a container or delivery device. The incorporation of gas bubbles into a formable material can create both structural and aesthetic problems. Once the material is solidified, the gas bubbles form pores in the solid. These pores can reduce the structural integrity of the final product. If the pores are visible, they can also reduce the aesthetic appeal of the product.

In dental materials, the presence of pores can weaken the final dental product, causing a greater tendency for the material to crack. Pores can also cause problems when polishing the dental product. Polishing into a pore will result in a ridge or groove in the surface of the product. In addition, if large enough, the pores can be visible in the dental product, which is often translucent. Visible pores in dental materials can be objectionable to patients.

The gas incorporated into a formable material can be removed by certain methods known to the art, including centrifuging. However these prior art methods have disadvantages. Centrifuging is time consuming and can result in the separation of different components of a material. For example, when dental composite materials are centrifuged, the resin component of the composite can separate from the filler component. Centrifuging results in the pressure being applied in a non-uniform manner. The pressure exerted on a particular sample, and within the sample itself, will vary depending on the location of the sample in the centrifuge. Also, centrifuging does not address the problem of air bubbles incorporated into the composite material while loading the material into a container or delivery device. Composite materials are often provided to a dentist in a syringe.

Another method of removing air bubbles is suggested in U.S. Pat. No. 5,328,262. In this method, bone cement is subjected to a partial vacuum during the mixing process in order to reduce its porosity. The need for a partial vacuum in the manufacturing process increases the time and expense of producing the material. Furthermore, this method does not eliminate air bubbles incorporated into the material while loading it into a container.

Thus, there exists in the art a need for a simple and expedient way to reduce or eliminate the number and size of gas bubbles in a formable material, especially once the material has been placed in a container. In particular there is a need to reduce the amount of air bubbles in a composite material contained in a syringe.

SUMMARY OF THE INVENTION

The present invention provides methods to reduce the number and/or size of gas bubbles present in a formable material. The material can generally be any material, and a presently preferred material is a composite material. One class of composite material suitable for use in the inventive methods are dental composites.

According to one embodiment, the components of a dental composite are mixed together and then loaded into a container, such as a syringe. The container is then placed in a pressurizing chamber, or alternatively can be loaded with composite within the pressurizing chamber. The container is subjected to one or more periods of pressurization. The pressurization results in fewer and/or smaller air bubbles in the composite. The composite material in the container can then be provided to a dentist who can use the material for the desired application. The methods of the present invention result in greater ease of production of a composite material having a reduced amount of porosity. The materials produced by the methods of the present invention can have enhanced physical characteristics such as greater flexural strength and better polishability.

DESCRIPTION OF THE FIGURES

The following FIGURE forms part of the present specification and is included to further demonstrate certain aspects of the present invention. The invention may be better understood by reference to this FIGURE in combination with the detailed description of specific embodiments presented herein.

| Figure | Description |
| --- | --- |
| 1 |

DETAILED DESCRIPTION OF THE INVENTION

Figures 1A, 1B:
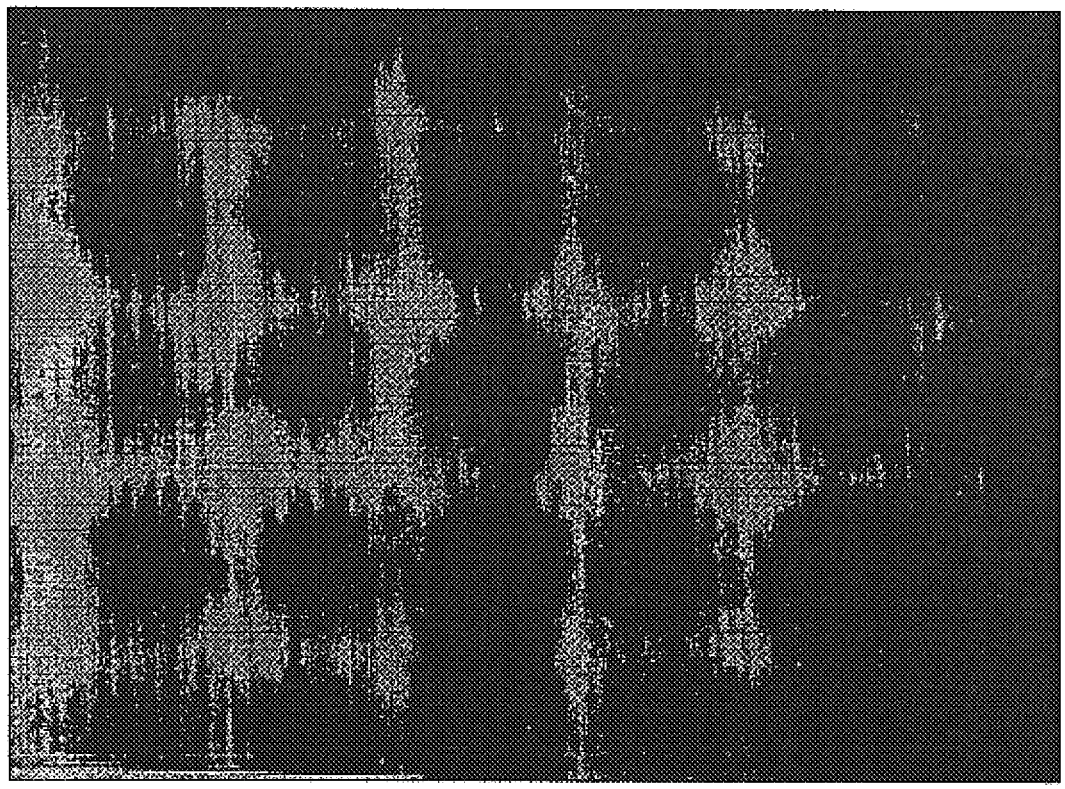
FIG. 1 is a photograph of a dental composite produced using the methods of the present invention (FIG. 1A) and a control (FIG. 1B). The photograph was taken while viewing the specimens under a light microscope (at 100 .times. magnification). The surface of the specimens was smeared with blue dye to show exposed bubbles. |

One aspect of the present invention are methods of reducing the number and/or size of gas bubbles in a material by subjecting the material to pressure. The methods of the present invention can be practiced using any flowable material, including materials such as composites, putties, pastes, caulks and gels. According to one embodiment of the invention, the material is a composite. According to a more specific embodiment, the composite is a dental composite. Examples of suitable dental composites are the TESCERA™, RENEW®, MICRONEW™, AELITE™ LS and AELITEFIL™ composite materials, products of Bisco, Inc. (TESCERA™, MICRONEW™, AELITE™ LS and AELITEFIL™ are trademarks of Bisco, Inc. RENEW® is a registered trademark of Bisco, Inc.).

Other composites that can be used include PRODIGY™ and HERCULITE® XRV™, available from Kerr Corp. (PRODIGY™ and XRV™ are trademarks of Kerr Corp, HERCULITE® is a registered trademark of Kerr Corp.); Z100™ and Z250™, available from 3M Co. (Z100™ and Z250™ are trademarks of 3M Co.); DIAMONDCROWN™ and DIAMONDLITE™, available from Biodent (DIAMONDCROWN™ and DIAMONDLITE™ are trademarks of Biodent); HELIOMOLAR®, available from Ivoclar Vivadent AG (HELIOMOLAR® is a registered trademark of Ivoclar Vivadent AG); and VIT-L-ESCENCE®, available from Ultradent Products, Inc. (VIT-L-ESCENCE® is a registered trademark of Ultradent Products, Inc.).

Generally any composites can be used in the present invention. Composites can comprise a resin component and a filler component. The filler component can be sintered or ground glass. The resin component can be a dimethacrylate. Suitable dimethacrylates include triethyleneglycol dimethacrylate, bisphenol "A" diglycidyl methacrylate, ethoxylated bisphenol "A" dimethacrylate and urethane dimethacrylate.

When the material to be used is a dental composite material, any components of the material, and any components to be incorporated with that material, can be mixed together. According to one embodiment, the material is contained within a suitable container or delivery device. One of skill in the art will be capable of determining what container or delivery device can be used for a particular application. Such containers and delivery devices should be capable of withstanding the pressures to be employed in the methods of this invention. Such containers can be non-airtight. Suitable containers include bags, beakers, flasks, test tubes, bowls, plates, wells, dishes, glasses, tubs, and buckets. Other suitable containers include syringes, tubes for use in syringes (such as those available from Techon Systems, Inc.) and C/R® tubes (available from Centrix, Inc., C/R® is a registered trademark of Centrix, Inc.). The containers and delivery devices can be made from any suitable material, including metal, stainless steel, ceramic, plastic, and glass.

The container or delivery device containing the material is subjected to pressure for one or more periods of time sufficient to remove the desired amount of gas bubbles. As opposed to the non-uniform pressure exerted by a centrifuge, the present invention involves pressurizing the environment of the composite.

The two primary variables to be manipulated are the time the material is subjected to the pressure and the magnitude of the applied pressure. The particular time and pressure needed to remove the desired amount of gas bubbles from a material will depend on the nature of the material. The extent to which gas bubbles are to be removed will also affect the time and pressure needed to achieve the desired result. Generally, more time and/or greater pressure will be required to remove a greater proportion of gas from a given material.

Generally, if a smaller difference between ambient pressure and the treatment pressure is to be used, the time the sample is exposed to the pressure can be increased in order to achieve the same level of gas removal. If the time of exposure is to be decreased, the difference in pressure can be increased accordingly.

The pressure applied can be higher or lower than ambient pressure. Those of skill in the art will recognize that different types of materials will require different amounts of pressure in order to remove porosity within a given time. All pressures reported in this disclosure are in pounds per square inch above ambient pressure (psi gauge; psig) unless specified otherwise. Presently preferred pressures are higher than ambient pressure, for example about 15 psi (0.1034 MPa), about 20 psi (0.1370 MPa), about 30 psi (0.2068 MPa), about 45 psi (0.3103 MPa), about 60 psi (0.4137 MPa), about 80 psi (0.5516 MPa), about 100 psi (0.6895 MPa), about 120 psi (0.8274 MPa), about 140 psi (0.9653 MPa), about 180 psi (1.241 MPa), about 250 psi (1.724 MPa), about 500 psi (3.447 MPa), and about 1000 psi (6.895 MPa) above ambient pressure. For dental composite materials, such as TESCERA™ composites, it is presently preferred to use pressures of at least about 60 psi (0.4137 MPa) above ambient pressure. In particular, a pressure of about 80 psi above ambient pressure is presently preferred.

Different materials will need to be subjected to a given pressure for varying amounts of time in order to remove a desired amount of porosity, depending on the nature of the material. For example, the viscosity and thickness of the material can affect the amount of time required. Thicker or more viscous materials may require longer treatment times. Some samples may only need to be subjected to a pressure for times on the order of seconds. Other materials may require longer times, for example about 5, about 10, about 15, about 20, about 30, about 45, about 60, about 90, or about 120 minutes. Some materials may require still longer times, for example about 4, about 8, about 12, about 16, about 24, about 36, about 48, about 60, or about 72 hours. For dental composite materials, such as TESCERA™ composites, it is presently preferred to subject the composite to a pressure of at least about 80 psi (about 0.5516 MPa) for at least about 20 minutes. The composite can be subjected to a pressure of about 80 psi (about 0.5516 MPa) for about 20 to about 60 minutes. Once again, those of skill in the art will recognize that typically when a greater pressure is used, the time required to remove a given amount of porosity from a sample will decrease.

The sample can be subjected to pressure for one time period, or for successive periods of time. For example, a sample can be subjected to pressure several times, interrupted by periods where the sample is maintained at atmospheric pressure. Alternatively, the pressure can be increased or decreased in a stepwise fashion, holding at a particular intermediate step or steps for whatever period of time is desired. The pressure can also be increased or decreased more gradually.

In one embodiment, which is presently preferred for dental materials such as TESCERA™ composites, the pressure container undergoes several purge cycles where the pressure returns to the initial, lower pressure. The purge can be achieved by any number of means, including by introducing a gas, such as air or nitrogen, into the sample chamber. The purge cycles are followed by a pressure soak where the sample is maintained at the higher pressure for a period of time. In a particular presently preferred embodiment, the pressure device undergoes six purge cycles followed by a pressure soak. Other variations of these factors will be recognized by those skilled in the art and can be chosen to meet the particular requirements of a sample.

The pressure can be applied at various times during the preparation of the material without departing from the scope of the present invention. For example, the components of a material could be mixed together under ambient pressure, and then the mixture could be subjected to pressure treatment in order to remove gas bubbles. Alternatively, the components of the material could be pressurized prior to or during mixing. The components or material could be pressurized or at ambient pressure and introduced into a container that was already pressurized. The introduction can be performed in a batch operation or a continuous operation.

The temperature of the sample, or of the pressure applying device, may have an effect on the pressure and time required to remove the desired amount of gas from a sample. The temperature can be adjusted as desired by the person of skill in the art without departing from the scope of the present invention. A change in temperature may require more or less time or pressure in order to achieve the same level of gas removal. In general, use of higher temperatures will shorten the required treatment time.

Treatment of materials by the methods disclosed herein preferably reduce the number and/or volume of gas bubbles present in the material. The total volume of gas bubbles present in the material after treatment is preferably reduced at least about 10%, about 20%, about 40%, about 60%, about 80%, about 90%, about 95%, about 99%, and ideally about 100%.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Modification of NTL Unit to Pressurize Composites Following Mixing

An NTL™ unit (NTL™ is a trademark of Bisco, Inc.) can be modified to serve as a pressure chamber by simply removing the lamp, located under the top dome of the chamber, and connecting a compressed air line to the nitrogen port. If the user wants to pressurize the composite using nitrogen gas instead of compressed air, the nitrogen line is left attached to the NTL. A sample of composite is placed in the chamber, the chamber is sealed, and a cycle is started. The NTL will cycle through 6 purges leaving the chamber pressurized at the pressure of the gas at the inlet port. The time of pressurization is controlled by the user, as the NTL will remain at pressure indefinitely. When the desired treatment time has elapsed, the NTL is turned off. The chamber will vent, allowing access to the pressure-treated composite.

Example 2

Production of a Dental Composite Having Reduced Porosity

Three syringes were filled with TESCERA™ Incisal Transparent composite material (available from Bisco, Inc.) which had been hand kneaded to incorporate air into the composite. The three syringes were then placed in a modified NTL™ pressure chamber unit (Example 1). The NTL™ chamber was set for 80 psi nitrogen gas, and the composite was left in the chamber for 20 minutes. During the 20 minutes, the pressure chamber went through 6 purge cycles before the pressure soak. After 20 minutes, the syringes were removed from the pressure chamber and the composite material was extruded from the syringes. Composite material was also extruded from a syringe that was not subjected to the pressure treatment (control sample). The extrusions were cured using a V.I.P.™ device (V.I.P.™ is a trademark of Bisco, Inc.), and then ground lengthwise. The material subjected to the pressure treatment contained practically no bubbles. The material that was not subjected to the pressure treatment (control sample) contained many bubbles that were visible to the naked eye.

Example 3

Preparation of Photographs Comparing Pressurized Composite and Control

Two syringes were filled with composite material following the procedure of Example 2. One syringe was pressure treated and underwent 6 purges at 80 psi air followed by a 30 minute pressure soak. The second syringe was left at ambient pressure. The contents of each syringe were then extruded and light cured. The cylinder shaped cured composites were ground down to a flat surface. Blue dye was spread across the flat surfaces to aid in visual identification of pores. Polaroid photographs were taken while viewing the two composite surfaces through a light microscope (at 100× magnification). As can be seen in FIG. 1, the cured composite of the pressure treated sample had significantly fewer bubbles than did the control.

Example 4

Measurement of Physical Properties of Pressurized and Control Composites

The structural properties of the pressurized and control composites prepared in Example 3 were evaluated. Ten specimens each of the pressurized and control samples were prepared and analyzed using a QTest universal testing machine (available from MTS Systems Corp.). The flexural strength and elastic modulus were determined for each sample. The testing technique used was that set forth in ANSI/ADA Specification 27 (available from Standards Administration, American Dental Association, 211 E. Chicago Avenue, Chicago, Ill. 60611). The results of these tests are presented in Table 1. As Table 1 shows, the flexural strength of the pressured composite was significantly higher than that of the control. However, the elastic modulus values obtained for the control and the pressurized composite were similar. This result is consistent with both materials having a similar stiffness. The flexural strength and elastic modulus values indicate that the pressurized composite will have similar stiffness and formability properties to the control composite, preserving desirable properties in a dental composite, yet the pressurized composite will have greater flexural strength.

TABLE 1

Physical Properties of Pressurized and Control Composites

| Sample | Flexural Strength (mean, standard deviation) (MPa) | Elastic Modulus (mean, standard deviation) (GPa) |
| --- | --- | --- |
| Control | 74 (7) | 8.7 (0.1) |
| Pressurized | 133 (14) | 8.7 (0.2) |

Example 5

Modification of Ross Mixer to Pressurize Composites While Mixing

Ross-type mixers can be ordered with airtight seals and required plumbing for vacuum or pressurization of the mixing bowl. An air compressor can be connected to the vacuum port. While the composite is being mixed, the chamber can be brought to any desired pressure by the air compressor and sealed off.

All of the processes and methods disclosed and claimed herein can be made and executed without undue experimentation in light of the present disclosure. While methods of this invention have been described in terms of preferred embodiments, it will be apparent to those of skill in the art that variations may be applied to the methods and processes and in the steps or in the sequence of steps of the methods described herein without departing from the concept, spirit and scope of the invention. All such similar substitutes and modifications apparent to those skilled in the art are deemed to be within the spirit, scope and concept of the invention.

What is claimed is:

1. A method for removing gas bubbles from a flowable dental material, the method comprising applying gas pressure to the flowable dental material for a time period sufficient to reduce the volume of gas bubbles in the flowable dental material.

2. A method for removing gas bubbles from a flowable dental composite material, the method comprising applying gas pressure to the flowable dental composite material for a time period sufficient to reduce the volume of gas bubbles in the flowable dental composite material.

3. The method of claim 2, wherein the pressure is greater than ambient pressure.

4. The method of claim 2, wherein the pressure is cycled between two or more pressures during the time period.

5. The method of claim 2, wherein the material is formable.

6. The method of claim 2, wherein the material comprises a filler and a resin.

7. The method of claim 2, wherein: the material comprises a resin and a filler; and the filler is ground glass or sintered glass.

8. The method of claim 2, wherein: the material comprises a filler and a resin; and the resin comprises a dimethacrylate.

9. The method of claim 2, wherein: the material comprises a filler and a resin; and the resin is selected from the group consisting of triethyleneglycol dimethacrylate, bisphenol "A" diglycidyl methacrylate, ethoxylated bisphenol "A" dimethacrylate and urethane dimethacrylate.

10. The method of claim 2, wherein the material is comprised in a container.

11. The method of claim 2, wherein the material is comprised in a delivery device.

12. The method of claim 2, wherein the material is comprised in a syringe.

13. The method of claim 2, wherein the material is comprised in a tube.

14. The method of claim 2, wherein the pressure is at least about 60 psi above ambient pressure.

15. The method of claim 2, wherein the pressure is at least about 80 psi above ambient pressure.

16. The method of claim 2, wherein the time period is at least about 20 minutes.

17. The method of claim 2, wherein the pressure is cycled between about 80 psi above ambient pressure and ambient pressure.

18. The method of claim 17, wherein the pressure is cycled about six times.

19. The method of claim 2, further comprising changing the temperature of the material during the time period.

20. A method for preparing a dental composite, the method comprising: mixing the components of the dental composite to form a flowable mixture; and applying gas pressure to the mixture for a time period sufficient to reduce the volume of gas bubbles in the flowable mixture.

21. The method of claim 20, wherein the mixing of the components and the applying of the pressure to the mixture occur simultaneously.

22. The method of claim 20, wherein the pressure is higher than ambient pressure.

23. The method of claim 20, wherein the composite is formable.

24. The method of claim 20, wherein the composite comprises a filler and a resin.

25. The method of claim 20, wherein: the composite comprises a resin and a filler; and the filler is ground glass or sintered glass.

26. The method of claim 20, wherein: the composite comprises a filler and a resin; and the resin comprises a dimethacrylate.

27. The method of claim 20, wherein: the composite comprises a filler and a resin; and the resin is selected from the group consisting of triethyleneglycol dimethacrylate, bisphenol "A" diglycidyl methacrylate, ethoxylated bisphenol "A" dimethacrylate and urethane dimethacrylate.

28. The method of claim 20, wherein the pressure is cycled between two or more pressures.

29. The method of claim 20, wherein the composite is comprised in a container.

30. The method of claim 20, wherein the composite is comprised in a delivery device.

31. The method of claim 20, wherein the composite is comprised in a syringe.

32. The method of claim 20, wherein the composite is comprised in a tube.

33. The method of claim 20, wherein the pressure is at least about 60 psi above ambient pressure.

34. The method of claim 20, wherein the pressure is at least about 80 psi above ambient pressure.

35. The method of claim 20, wherein the pressure is applied for at least about 20 minutes.

36. The method of claim 20, wherein the pressure is cycled between about 80 psi above ambient pressure and ambient pressure.

37. The method of claim 36, wherein the pressure is cycled about 6 times.

38. The method of claim 20, further comprising changing the temperature of the composite during pressurization.

* * * * *